US005218112A

United States Patent [19]

Reardan et al.

[11] Patent Number: 5,218,112

[45] Date of Patent: Jun. 8, 1993

[54] LINKING AGENTS AND METHODS

[75] Inventors: Dayton T. Reardan, Hercules; Dane A. Goff, Menlo Park, both of Calif.

[73] Assignee: Xoma Corporation, Berkeley, Calif.

[21] Appl. No.: 573,615

[22] Filed: Aug. 27, 1990

Related U.S. Application Data

[62] Division of Ser. No. 151,700, Feb. 3, 1988, Pat. No. 4,970,303.

[51] Int. Cl.⁵ ...................... C07D 213/72; C08B 37/00

[52] U.S. Cl. .................................... 540/471; 536/124; 540/472; 540/473; 546/294; 548/166; 548/307.1

[58] Field of Search ........................ 540/471, 472, 473; 546/294; 548/166, 304; 564/163, 192, 500

[56] References Cited

U.S. PATENT DOCUMENTS

| | | | |
|---|---|---|---|
| 4,508,906 | 4/1985 | Bamberg et al. | 548/166 |
| 4,666,503 | 5/1987 | Shiokawa et al. | 548/166 |
| 4,845,108 | 7/1989 | Young et al. | 546/294 |
| 4,889,866 | 12/1989 | Pfister et al. | 546/294 |
| 4,952,235 | 8/1990 | Andree et al. | 546/294 |
| 4,970,303 | 11/1990 | Reardan et al. | 536/124 |
| 4,975,448 | 12/1990 | Schoenwald et al. | 548/166 |

*Primary Examiner*—Ronald W. Griffin

*Attorney, Agent, or Firm*—Townsend and Townsend

[57] ABSTRACT

Compounds containing carbohydrate moieties or carboxyl groups are linked to either compounds containing thiol moieties or electron-deficient moieties by the use of linking agents of the formula

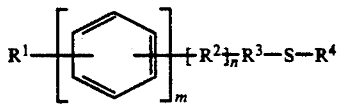

in which $R^1$ is $NH_2$— or $NH_2$—NH—; $R^2$ is —NH—C(O)—, —C(O)—NH—, or —C(O)—; $R^3$ is $C_1$-$C_{10}$ alkylene, $C_5$-$C_7$ cyclic alkylene, arylene, phenyl-substituted $C_1$-$C_{10}$ alkylene, benzyl-substituted $C_1$-$C_{10}$ alkylene, or amino-substituted $C_1$-$C_{10}$ alkylene; $R^4$ is H, acetyl,

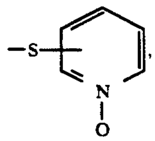

, 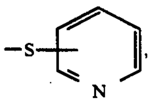 ,

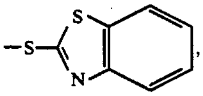

, or 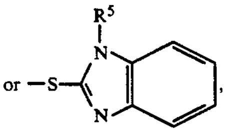 , where $R^5$ is $C_1$-$C_5$ alkyl; m is zero or 1; and n ia zero or 1.

29 Claims, No Drawings

LINKING AGENTS AND METHODS

This is a continuation of application Ser. No. 07/151,700, filed Feb. 3, 1988, now U.S. Pat. No. 4,970,303.

BACKGROUND OF THE INVENTION

This invention relates to the formation of conjugates, and in particular to the joining of one species to another at a carbohydrate or carboxyl moiety on one of the species, utilizing a thioether or disulfide bond as part of the linkage.

The linkage of compounds of various types to carbohydrate or carboxyl moieties is desirable for a variety of reasons. In the formation of conjugates involving immunoglobulins, for instance, linkage at specific regions on the immunoglobulin is often desirable for purposes of maintaining the accessibility of antigen-binding sites or of sites on the Fc chains for complement binding. As a further example, certain solid supports used in affinity chromatography have carbohydrate or carboxyl groups available for binding, and the same is true for other solid phase materials as well such as those used in two-phase immunoassays.

Many of the species which are sought to be linked to these carbohydrate or carboxyl moieties are species which lack the ability to react directly.

SUMMARY OF THE INVENTION

Novel compositions and methods are provided herein for the formation of linkages of the type described above at carbohydrate or carboxyl moieties. The novel compositions are linking agents falling within the following generic formula:

Formula I:

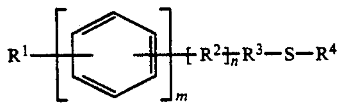

in which $R^1$ is a member selected from the group consisting of $NH_2$ and $NH_2$—NH—;

$R^2$ is a member selected from the group consisting of —NH—C(O)—, —C(O)—NH—, and —C(O)—;

$R^3$ is a member selected from the group consisting of $C_1$-$C_{10}$ alkylene, phenylsubstituted $C_1$-$C_{10}$ alkylene, benzylsubstituted $C_1$-$C_{10}$ alkylene, aminosubstituted $C_1$-$C_{10}$ alkylene, $C_5$-$C_7$ cyclic alkylene and arylene; and $R^4$ is a member selected from the group consisting of H, acetyl,

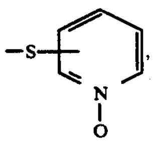, 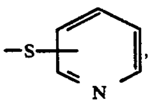,

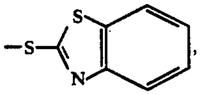, and 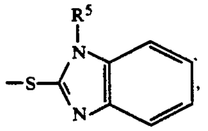, where $R^5$ is $C_1$-$C_5$ alkyl:

m is zero or 1; and n is zero or 1.

Within the scope of this formula, certain embodiments are preferred, notably those of the formulas given below. (In each of these formulas, $R^1$, $R^3$, and $R^4$ are as defined above.)

Formula II:

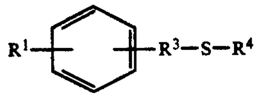

Formula III:

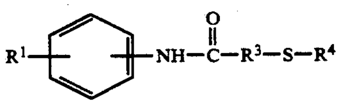

Formula IV:

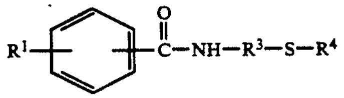

Formula V:

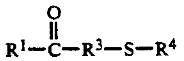

In each of these formulas, the terms "alkylene" and "alkyl" refer to saturated divalent and monovalent hydrocarbon radicals, respectively, and are intended to include straight-chain, branched-chain and cyclic structures. Examples of alkylene groups are $—CH_2—$, $—CH_2—CH_2—$, $—CH_2—CH_2—CH_2—$ and longer chains; and $—CH(CH_3)—$, $—C(CH_3)_2—$, $—CH(CH_3)—CH_2—$, $—CH(CH_3)—CH(CH_3)—$, $—CH(CH_3)_2—CH_2—$,

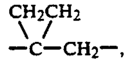

and the reverses thereof (i.e., left-to-right). Preferred alkylene groups are those having 1 to 6 carbon atoms, the most preferred being those having 1 to 4 carbon atoms.

The term "cyclic alkylene" refers to a saturated divalent cyclic hydrocarbon radical, with the two points of attachment being at any two locations on the ring. Examples are cyclopentylene, cyclohexylene, and cycloheptylene. A preferred group is 1,2-cyclohexylene (in which the two points of attachment are on adjacent carbon atoms on the ring).

The term "arylene" refers to a divalent radical containing at least one aromatic ring, with the two points of attachment being at any two locations on the ring (or rings, in the case of multi-ring groups). Examples are phenylene, particularly 1,2-phenylene, and naphthylene.

In Formulas I, II, III and IV, the two points of attachment on the phenyl ring may be ortho-, meta- or para- with respect to each other. Compounds in which the points of attachment are meta- or para- are preferred, with para- the most preferred. In the $R^4$ definition, the sulfur substituent on the pyridine and pyridine N-oxide may be in the 2-, 3-, or 4-position. The 2- and 4-positions are preferred, with the 2-position being the most preferred.

The following are examples of compounds within these formulas:

S-acetyl-4-(4-aminophenyl)-1-butanethiol
S-acetylthioacetic acid, 4-aminoanilide
2-pyridyl-3'-propanoyl disulfide, 4-aminoanilide
S-acetylthioacetic acid hydrazide
2-pyridyl-3'-propanoyl disulfide hydrazide
2-pyridyl-1'-methyl-3'-propanoyl disulfide hydrazide
2-pyridyl-1',1'-dimethyl-3'-propanoyl disulfide hydrazide
2-pyridyl-1',2'-dimethyl-3'-propanoyl disulfide hydrazide
2-pyridyl-2',2'-dimethyl-3'-propanoyl disulfide hydrazide
2-pyridyl 1'-(2'-ethanoyl)-cyclopropane disulfide hydrazide
2-pyridyl-1',1'-dimethyl-2'-amino-3'-propanoyl disulfide hydrazide
2-pyridyl-1'-isopropyl-2'-ethanoyl disulfide hydrazide
2-pyridyl-1'-phenyl-2'-ethanoyl disulfide hydrazide
2-pyridyl-1'-methyl-2'-ethanoyl disulfide hydrazide
2-pyridyl-1',1'-dimethyl-2'-ethanoyl disulfide hydrazide
2-pyridyl 1'-(2'-ethanoyl)-cyclohexane disulfite hydrazide
2-pyridyl 1'-(2'-ethanoyl)-cycloheptane disulfide hydrazide The invention further extends to water-soluble salts and derivatives of these compounds. The salts may be formed by anionic moieties to complement the amine (or hydrazine) terminus of the compounds in cationic form. Examples of such salts are acetate salts, trifluoroacetate salts, hydrohalide salts, particularly hydrochloride and hydrobromide salts, and toluenesulfonic acid salts. The derivatives may be compounds having the same formula but with the addition of a charge group at a point on the molecule where it does not interfere with the coupling ability of either of the end groups on the molecule. Examples of such derivatives are those bearing sulfonic acid ($—SO_3—$) groups and those bearing nonreactive amino groups (such as diethylamino, for example). The most preferred among these are the trifluoroacetate salts.

DETAILED DESCRIPTION OF THE INVENTION AND PREFERRED EMBODIMENTS

The compounds of the present invention are prepared by conventional techniques well known among those skilled in the art, selected in accordance with the desired substituent groups of the formulas as listed above. Compounds with aminophenyl terminal groups (as in Formulas II, III and IV with $R^1=NH_2—$), for instance, may be prepared from the corresponding nitrophenyl analogs by reduction. An example is reduction with stannous chloride. Compounds where $R^1$ is a hydrazino group may be prepared from an N-protected hydrazino starting material or an appropriately substituted carbazate.

Compounds of Formula II may be prepared from the corresponding nitrophenyl alcohols. Compounds of Formula III with an amino group as $R^1$ may be prepared by reacting an appropriately substituted N-hydroxysuccinimide ester with an appropriately substituted 4-aminoaniline. Other standard coupling methods for this formula may also be used.

Compounds with a carbonylaminomethylene group may be prepared by coupling an N-protected amino benzoic acid with the appropriate amino disulfide or S-protected amino thiol. Compounds of Formula IV with a hydrazino group as $R^1$ may be prepared by coupling an N-protected hydrazino benzoic acid with the appropriate thiol-containing amine. Compounds of Formula V with a hydrazino group as $R^1$ may be prepared by coupling a thiol-containing carboxylic acid with an appropriately substituted carbazate.

The preparation of other compounds within these formulas, as well as the derivatives described above, is done with the appropriate variations on the above, as will be readily apparent to those skilled in the art.

Salts are readily prepared by conversion of the compounds in carbamate form with the appropriate acids, and the free base may be formed by treatment with base.

These compounds are useful in placing a sulfhydryl or disulfide functional group at the site of a carbohydrate group or a carboxyl moiety on another compound, and likewise for linking two compounds at specified functional groups, i.e., a carbohydrate or carboxyl moiety on one and a thiol or electron-deficient moiety on the other. In the case of the thiol moiety, the reaction at the corresponding end of the linking agent will produce a disulfide group, preferably by disulfide exchange. In the case of an electrondeficient moiety (such as maleimide or an α-halo carbonyl group), the reaction will be a nucleophilic displacement or addition reaction.

The utility of these linking agents is in providing linkages between species in a site-specific manner with respect to at least one of the species, and in some cases with site specificity on both species. These agents may thus be used for example in linking proteins or other molecules to carbohydrates or carboxyl groups on other proteins or substances such as column supports and glass, or any substance containing the particular types of functional groups with which phenylamines, hydrazines or hydrazides will react. They can also be used to introduce a sulfhydryl moiety for purposes of site specificity for reaction with an electron-deficient moiety of another species, such as for example an ethylene group between two highly electronegative groups (i.e., maleimide).

The linking reactions used to form these linkages may be done according to conventional techniques well known among those skilled in the art. In the case of a species containing a carbohydrate moiety, the carbohydrate is first converted to an aldehyde. It is then reacted with the amino terminus of the linking agent in accordance with known conventional reaction conditions to form an imine or hydrazone linkage which can then be reduced if necessary. When more than one carbohydrate moiety is present on the species, certain specific carbohydrates may be selectively oxidized in some cases, depending on the type of molecule bearing the carbohydrate groups. In the case of immunoglobulins, for instance, carbohydrate side chains may be selectively oxidized by the use of galactose oxidase or periodate under mild conditions. The reaction at the other end of the linking agent, as mentioned above, will depend on whether the reaction is one of disulfide exchange or nucleophilic displacement. In either case, conventional procedures known to those skilled in the art may be used.

In the case of a species containing the carboxyl moiety the amino terminus of the linking agent is coupled to form an amide bond.

A wide variety of pairs of species may be linked by the linking agents of the present invention. Examples are proteins and macromolecules in general, linked to other proteins or macromolecules or to smaller molecular species, such as bifunctional chelators, luminescent agents and NMR shift reagents. A particularly useful example is the coupling of immunoglobulins at the Fc region to toxins or labels to impart the site specificity characteristic of the immunoglobulin to the toxin or label. Examples of such labels are enzymes, radioisotopes (through bifunctional chelators), and fluorescent agents (also possibly through bifunctional chelators).

The following examples are offered for purposes of illustration, and are intended neither to limit nor define the invention in any manner. In these examples, the following abbreviations are used:

NMR: nuclear magnetic resonance at 60 MHz; all chemical shifts given in δ values relative to tetramethylsilane: "s"=singlet, "br s"=broad singlet, "d"=doublet, "t"=triplet, "m"=multiplet, "ar."=aromatic
IR: infrared spectra; values given in $cm^{-1}$; "sh" =shoulder, "br"=broad
LRMS: low resolution mass spectroscopy, intensity given relative to the base peak
TLC: thin-layer chromatography: values given in $R_f$ (ratio to the front)
UV/VIS: ultraviolet/visible spectra: values given in relative absorption
TFA: trifluoroacetic acid
EtOAc: ethyl acetate
Ac: acetyl
s.m.: starting material

EXAMPLE 1

Preparation of S-Acetyl-4-(4-aminophenyl)-1-butanethiol

This example illustrates the preparation of one of the compounds within the scope of the present invention. S-acetyl-4-(4-aminophenyl)-1-butanethiol, whose structural formula is that of Formula I above, in which $R^1$ is 4-amino, $R^3$ is $-(CH_2)4-$ and $R^4$ is acetyl.

A solution of S-acetyl-4-(4-nitrophenyl)-1-butanethiol (1.0 g. 3.95 mMol) in 25 mL of methanol was heated in a bath at 60° C. under a nitrogen atmosphere with $SnCl_2.2H_2O$ (4.45 g, 19.8 mMol) for 6 hours. The composition was not changing after 4 hours (using thin-layer chromatography, hereinafter "TLC"), although some starting material still remained. (The product was observed to have a $R_f$ of 0.0 in a 90:10 mixture of hexanes and ethyl acetate, as opposed to a $R_f$ of 0.45 for the starting material.) An additional 0.60 g of $SnCl_2.2H_2O$ was then added. After 6 hours, the reaction mixture was cooled on ice and then brought to pH 7 with 100 mL of cold 50% saturated aqueous $NaHCO_3$.

A voluminous white precipitate formed. This was extracted with four 100 mL portions of ethyl acetate. The organic layers were rinsed with water, dried over $Na_2SO_4$, and concentrated in vacuo. NMR indicated the presence of the thioacetyl group (a positive indication of the existence of the desired product). The crude yield was 0.60 g (68%).

The crude product was subjected to flash chromatography on $SiO_2$, eluting with 90/10 hexanes/ethyl acetate to 80/20 hexanes/ethyl acetate. The major product eluted with 20% ethyl acetate and had a $R_f$ of 0.08 in 90/10 hexanes/ethyl acetate, yielding 300 mg of an oil (34% yield). Identity of the product as S-acetyl-4-(4-aminophenyl)-1-butanethiol was confirmed by NMR, TLC, IR, LRMS and UV/VIS as follows:

NMR ($CDCl_3$); 6.88 (d. 2H, ar.); 6.50 (d. 2H, ar.); 3.48 (s, 2H, $NH_2$) 2.85 (m, 2H, $CH_2$); 2.47 (m, 2H, $CH_2$); 2.32 (s, 3H, SAc); 1.57 (m, 4H, $2CH_2$)
IR (NaCl, neat); 3440, 3390 ($NH_2$); 2930, 1680 (s, SAc); 1618, 1528 ($NH_2$); 1278, 1135, 960, 830 (strong $NO_2$ absorbance at 1350 $cm^{-1}$ in s. m. gone)
LRMS: 223 (M+, 14.0%); 181 (M+, $-COCH_3$, 22.0%); 106 (100%)
TLC (90/10 hexanes/EtOAc); $R_f$ 0.08 (ninhydrin positive)
UV/VIS: ($CHCl_2$) 296 (0.33), 250 (1.41); ($CH_3OH$) 288 (0.05), 234 (0.69), 214 (0.85)

EXAMPLE 2

Preparation of 4-(4-Aminophenyl)-1-butanethiol

The structural formula of this compound corresponds to that of Formula I above, in which $R^1$ is 4-amino, $R^3$ is $-(CH_2)4-$ and $R^4$ is H.

A solution of S-acetyl-4-(4-aminophenyl)-1-butanethiol (1.3 g. 5.8 mMol) in ethanol (25 mL) was stirred with 1M aqueous ammonia (25 mL) at room temperature in the dark under nitrogen overnight. The pH was then adjusted to 6.0 with 2M HCl and the solution extracted with three 75-mL portions of EtOAc. The organic layers were rinsed with water dried over $Na_2SO_4$ and concentrated in vacuo to give a pale yellow liquid weighing 0.94 g (90% yield). The identity of the product as 4-(4-aminophenyl)-1-butanethiol was confirmed by NMR, TLC, IR and UV/VIS as follows:

NMR ($CDCl_3$); 6.92 (d, 2H, ar.); 6.53 (d. 2H, ar.); 3.53 (s, 2H, $NH_2$); 2.28–2.75 (m, 4H); 1.08–1.92 (m, 5H)
IR (NaCl, neat); 3440, 3360, 3020, 2930, 2860, 1620 (s), 1515 (s), 1435, 1280 (s), 1185, 1130, 830
TLC (50/50 hexanes/EtOAc): $R_f$ 0.65
UV/VIS: ($CH_2Cl_2$) 296 (0.261), 246 (1.05); ($CH_3OH$) 290 (0.147), 238 (1.02), 210 (0.702)

EXAMPLE 3

Preparation of 2-Pyridyl-4'-[1-(4-aminophenyl)]butyl Disulfide

The structural formula corresponds to that of Formula I above, in which $R^1$ is 4-amino, $R^3$ is $-(CH_2)_4-$ and $R^4$ is 2-pyridylthio. A solution of 4-(4-aminophenyl)-1-butanethiol (0.94 g, 5.2 mMol) in EtOAc (20 mL) was treated with 2,2'-dipyridyldisulfide (1.15 g. 5.2 mMol) as a solid. After all the solid had dissolved, 4 drops of $BF_3.(C_2H_5)_2O$ was added and the solution was heated at a bath temperature of 55° C. The disulfide exchange was sluggish, so after 2 hours, 17 mL of benzene was added and the temperature was increased to 65° C. After a further 20 hours, the solvent was removed in vacuo and the crude product was purified on a chromatotron ($SiO_2$, Harrison Research), eluting with a step gradient of 5–20% EtOAc in hexanes. The mixed disulfide was obtained as a pale yellow oil weighing 0.41 g (27% yield). The identity of the product as 2-pyridyl-4'-[1-(4-aminophenyl)]butyl disulfide was confirmed by NMR. TLC and IR as follows:

NMR ($CDCl_3$); 8.45 (m. 1H, pyridyl); 7.42–7.82 (m, 2H, pyridyl); 6.75–7.18 (m, 1H, pyridyl); 6.92 (d, 2H, phenyl); 6.55 (d, 2H, phenyl); 3.58 (s, 2H, $NH_2$); 2.25–3.00 (m, 4H, $2CH_2$); 1.38–2.00 (m, 4H, $2CH_2$)
IR (NaCl, neat) 3430, 3340, 2930 (s), 1620, 1575, 1520, 1450, 1420, 1280, 1120, 830, 765
TLC (50/50 EtOAc/hexanes): $R_f$ 0.74

EXAMPLE 4

1. Preparation of S-Acetylthioacetic Acid. 4-(t-Butoxycarbonylamino)anilide

This compound was prepared as a precursor to the trifluoroacetate salt (described below).

A solution was prepared consisting of S-acetylthioacetic acid. N-hydroxysuccinimide ester (1.29 g. 5.6 mMol) and 4-(t-butoxycarbonylamino)aniline (1.5 g. 5.6 mMol) in ethyl acetate (30 mL). The solution was stirred at room temperature for 3.5 hours, then at 45° C. overnight. The reaction mixture remained colorless throughout.

The reaction mixture was then rinsed with two 50 mL portions of 10% saturated aqueous $NaHCO_3$, then with 50 mL of $H_2O$. The organic layers were dried over $Na_2SO_4$ and concentrated in vacuo to give a yellow oil. This was flash chromatographed twice on a $SiO_2$ column slurried in 50/50 ethyl acetate/petroleum ether, eluting with the latter as well. The fastest running fractions from each were pooled and concentrated. The resulting solid was recrystallized from methylene chloride/petroleum ether to give 1.22 g (67% yield) of a white solid with melting point 161°-162° C. The latter was identified as S-acetylthioacetic acid. 4-(t-butoxycarbonylamino)anilide by IR. NMR. UV/visible, and TLC, as follows:

NMR ($CDCl_3$): 8.00 (br s, 1H, NH); 7.33 (s, 5H, ar.); 6.55 (br s, 1H, NH); 3.65 (s, 2H, $CH_2$); 2.43 (s, 3H, SAc); 1,52 (s, 9H. t-butyl)

IR (KBr): 3350 (s), 1695 (s, SAc), 1660 (s, amide C═O) 1550 (s), 1410, 1315, 1235, 1170, 1065, 825, 705, 630

UV/VIS: ($CH_3OH$) 262 (0.597), 210 (0.518); ($CH_2Cl_2$) 270 (sh, 0.750), 258 (0.873)

TLC (50/50 EtOAc/hexanes); $R_f$ 0.75

2. Preparation of S-Acetylthioacetic Acid. 4-Aminoanilide, Trifluoroacetate Salt This compound has the structural formula of Formula III above, in which $R^1$ is 4-amino. $R^3$ is methylene, and $R^4$ is acetyl, in the form of the trifluoroacetate salt of the primary amine at the left end of the structure as shown.

The product of Section 1 of this example in the amount of 200 mg was dissolved in 5 mL of freshly distilled trifluoroacetic acid (hereinafter "TFA"). and stirred in the dark at room temperature under a nitrogen atmosphere for 1.5 hours. The solvent was then removed in vacuo at a temperature less than 30° C. to give a pale yellow oil in approximately quantitative yield. Its identity was confirmed as that of S-acetylthioacetic acid, 4-aminoanilide. trifluoroacetate salt by NMR as follows:

NMR ($D_2O$) 7.57 (d, 2H, ar.); 7.33 (d, 2H, ar.); 3.82 (s, 2H, $CH_2SAc$); 2.42 (s, 3H, SAc)

EXAMPLE 5

Preparation of 2-Pyridyl-3'-propanoyl Disulfide, 4-(t-Butoxycarbonylamino)anilide This compound was prepared as the precursor of the trifluoroacetate salt (described below).

A solution of 2,2'-dipyridyl disulfide (Aldrich. 1.5 g. 6.8 mMol) in 10 mL of dry ethyl acetate was treated with 3-mercaptopropionic acid (0.73 g. 6.89 mMol) in 10 mL of dry ethyl acetate. Then four drops of BF3.$(C_2H_5)_2O$ were added and the reaction stirred overnight at room temperature under a nitrogen atmosphere. The reaction was concentrated to dryness in vacuo, then slurried with 10 mL of cold ethyl acetate and filtered of all solid to give a pale yellow solution. To the latter were added 4-t-butoxycarbonylamino aniline (1.82 g, 6.8 mMol) in 10 mL of dry ethyl acetate and dicyclohexylcarbodiimide (1.40 g, 6.8 mMol). also in 10 mL ethyl acetate. The reaction was again stirred overnight at room temperature, then filtered to remove dicyclohexylurea. The filtrate was concentrated in vacuo, then subjected to flash chromatography on $SiO_2$, eluting with 30/70 ethyl acetate/hexanes.

A first fraction at $R_f$0.8 (with 50/50 ethyl acetate/-hexanes) was an oil not further characterized. A second fraction at $R_f$0.62 was a pale yellow solid, 0.48 g, identified by NMR as 4-t-butoxycarbonylamino aniline. A closely following third fraction at $R_f$0.50 was a solid, 0.66g (representing 23% yield) with melting point 139°-140° C. This was recrystallized from ethanol to yield a solid with a melting point of 154.5°-155.5° C. Its identity was confirmed as that of 2-pyridyl-3'-propanoyl disulfide. 4-(t-butoxycarbonylamino)anilide by NMR, IR. and elemental analysis, as follows:

NMR ($CDCl_3/CD_3OD$): 8.30 (m. 1H, pyridyl); 7.50-7.80 (m, 2H, pyridyl); 7.37 (s, 4H, phenyl ring); 6.87-7.27 (m, 1H, pyridyl); 3.00 (m, 2H); 2.75 (m, 2H); 1.50 (s, 9H, t-butyl)

IR (KBr): 3340 (Br); 1690,1655 (both C═O); 1520 (s), 1390, 1165, 1075, 842, 770

Elemental Analysis, found(required): C: 56.11(56.27), H: 5.83(5.72), N: 10.27(10.36), S: 15.75(15.81)

2. Preparation of 2-Pyridyl-3'-propanoyl Disulfide, 4-Aminoanilide, Trifluoroacetate Salt This compound has the structural formula of Formula III above, in which $R^1$ is 4-amino, $R^3$ is $-(CH_2)_2-$, and $R^4$ is 2-pyridylthio, in the form of the trifluoroacetate salt of the primary amine at the left end of the structure as shown.

A solution was prepared consisting of 150 mg of the product of Section 1 of this Example in 5 mL of freshly distilled TFA. The solution was stirred at room temperature under a nitrogen atmosphere for 1.5 hours in the dark. No yellow color (which would indicate liberated 2-pyridylthiol) was observed. The solvent was removed in vacuo at a temperature less than 30° C. to give a solid in quantitative yield. The solid was soluble in water, methanol and ethyl acetate, and its identity was confirmed as that of 2-pyridyl-3'-propanoyl disulfide, 4-aminoanilide, trifluoroacetate salt by proton NMR and UV/visible, as follows:

$^1H$ NMR ($D_2O$): 8.62 (m. 1H, pyridyl); 8.18 (m, 2H, pyridyl); 7.56-7.90 (m, partially obscured, 1H, pyridyl); 7.50 (pseudo-d, 4H, phenyl ring); 3.33 (t, 2H); 2.95 (t, 2H)

UV/VIS ($H_2O$): 242 (with poorly defined broad absorbance to about 310nm)

EXAMPLE 6

Preparation of S-Acetylthioacetic Acid, N-t-Butoxycarbonyl Hydrazide

This compound has the structural formula of Formula V above in which $R^1$ is hydrazino, $R^3$ is methylene, and $R^4$ is acetyl, in the form of the t-butyl carbamate.

A mixture of S-acetylthioacetic acid. N-hydroxysuccinimide ester (1.5 g,6.49 mMol) and t-butylcarbazate (0.86 g, 6.49 mMol) was stirred in dry ethyl acetate under a nitrogen atmosphere at room temperature for 24 hours, then at 60° C. for an additional 6.5 hours. The reaction mixture was then cooled on ice, rinsed with two 50 mL portions of saturated aqueous $NaHCO_3$ followed by water, then dried over $Na_2SO_4$ and concentrated in vacuo. A major product spot was observed by TLC (using 50/50 ethyl acetate hexanes) at $R_f$0.42.

The crude product was subjected to flash chromatography on $SiO_2$ eluting with 50/50 ethyl acetate/hexanes, which yielded a very pale yellow oil, 1.22 g (76% yield). Residual starting material was crystallized out, and the remaining mixture was concentrated to dryness, dissolved in 20 mL ethyl acetate. and rinsed with four 25 mL portions of 20% saturated aqueous $NaHCO_3$ followed by 25 mL of water, then dried over $Na_2SO_4$ and concentrated in vacuo to yield the final product, an oil whose identity was confirmed as that of S-acetylthioacetic acid. N-t-butoxycarbonyl hydrazide by NMR, IR, and UV/visible, as follows:

NMR ($CDCl_3$): 8.50 (br s, 1H, NH); 7.00 (br s, 1H, NH); 3.63 (s, 2H, $CH_2SAc$); 2.38 (s, 3H, SAc); 1.46 (s, 9H, t-butyl)

IR (NaCl, neat): 3290 (br), 2990, 1690 (br), 1490, 1375, 1255, 1165

UV/VIS: ($CH_2Cl_2$) 248; ($CH_3OH$) 218

This compound can be converted to the trifluoroacetate salt by procedures analogous to those described in the other examples in this specification. The compound may also be converted to other salts within the scope of the present invention by other conventional procedures.

EXAMPLE 7

Preparation of 2-Pyridyl-3'-propanoyl Disulfide, N-t-Butoxycarbonyl Hydrazide

This compound was prepared as a precursor of the trifluoroacetate salt (described below).

A solution of 2,2'-dipyridyl disulfide (3.8 g, 17 mMol) in 20 mL of ethyl acetate was treated with 1.8 g (17.2 mMol) of 3-mercaptopropionic acid in 10 mL of ethyl acetate and 5 drops of $BF_3.(C_2H_5)_2O$. The reaction mixture was stirred for 5 hours under nitrogen in the dark, then filtered and concentrated in vacuo. The resulting solid residue was slurried in 20 mL of cold ethyl acetate and refiltered. Then 1.98 g (15 mMol) of t-butylcarbazate was added, followed by 3.09 g (15 mMol) of dicyclohexylcarbodiimide in 10 mL of dry ethyl acetate. The reaction was stirred at room temperature for 18 hours in the dark, then filtered and concentrated in vacuo to yield a yellow oil. The oil was subjected to flash chromatography on $SiO_2$, eluting with 50/50 ethyl acetate/petroleum ether (35°-60° C.).

Three fractions were collected, the second containing the desired product at $R_f$0.40 (50/50 ethyl acetate/hexanes), 1.56 g (28% yield) of an oil, whose identity was confirmed as that of 2-pyridyl-3'-propanoyl disulfide, N-t-butoxycarbonyl hydrazide by NMR, IR, and UV/visible, as follows:

NMR ($CDCl_3$): 9.46 (br s, 1H, NH); 8.43 (m, 1H, pyridyl); 7.63 (m, 2H, pyridyl); 7.50 (br s, 1H, NH); 7.10 (q, 1H, pyridyl); 3.07 (m, 2H, $CH_2$) 2.77 (m, 2H, $CH_2$) 1.47 (s, 9H, t-butyl)

IR (NaCl, neat); 3280 (br), 2990, 1730 (sh), 1685 (br), 1420, 1372, 1250, 1165, 770

UV/VIS: $CH_2Cl_2$) 286 (1.05), 250 (1.30); ($CH_3OH$) 284 (0.74), 238 (1.49), 214 (sh. 1.11)

Preparation of 2-Pyridyl-3'-propanoyl Disulfide Hydrazide Trifluoroacetate Salt

This compound has the structural formula of Formula V above in which $R^1$ is hydrazino. $R^3$ is $—(CH_2)_2—$ and $R^4$ is 2-pyridylthio, in the form of the trifluoroacetate salt of the primary amine at the left end of the structure as shown.

A portion of the product of Section 1 of this Example (200 mg) was dissolved in freshly distilled TFA (5 mL) and stirred in the dark at room temperature under a nitrogen atmosphere for 1 hour, during which time a very faint pink color developed. The solvent was then removed in vacuo at a temperature less than 30° C. to give a pale yellow oil in approximately quantitative yield. The identity of the oil was confirmed as that of 2-pyridyl-3'-propanoyl disulfide hydrazide, trifluoroacetate salt by NMR, as follows:

NMR ($D_2O$); 8.73 (m, 1H, pyridyl); 8.33 (m, 2H, pyridyl), 7.88 (m, 1H, pyridyl); 3.23 (m, 2H, $CH_2$); 2.93 (m, 2H, $CH_2$)

EXAMPLE 8

Conjugate Preparation

This example illustrates the preparation of a conjugate of ricin A-chain with IND1 antibody through a carbohydrate moiety on the latter, using a linking agent in accordance with the present invention. The linking agent used is that prepared in Example 5, part 2. The following abbreviations are used in this example:

RTA: Ricin toxin A-chain
NaOAc: sodium acetate
DMSO: dimethyl sulfoxide
DTT: dithiothreitol
SDS PAGE: sodium dodecyl sulfide polyacrylamide gel electrophoresis
PBS: phosphate-buffered saline
SPDP: N-succinimidyl-3-(2-pyridyldithio)propionate
EIA: enzyme immunoassay 1. Periodate Oxidation of Carbohydrate Moiety on Antibody and Reaction With Linking Agent 1 mL of 5 mg/mL IND1 antibody in PBS was spun through a G-50 column equilibrated with 0.1 M NaOAc+0.15M NaCl, pH 5, and diluted 1:1 with 1 mL of 0.1M NaOAc buffer. The antibody was oxidized with 10 mM sodium periodate for 20 minutes at 0° C. in the dark, then quenched with 10 mM glycerol for 20 minutes at 0° C. in the dark. 250 μL of the quenched reaction was spun through G-50 into fresh acetate buffer. pH 5, then diluted 1:1 with acetate buffer to a final volume of 500 μL (3.3 μM).

A solution of the trifluoroacetate salt of 2-pyridyl-3'-propanoyl disulfide. 4-aminoanilide was prepared by combining 5-8 mg of the salt (which was a yellow oil) with 10 μL DMSO to give a 1.5-2M solution. This was then diluted about 50× with ethanol to produce 30mM 10× concentrated working stock solution. 55 μL of this solution was added to the reaction mixture described above, resulting in a final linking agent concentration of 300 μM (a linker:antibody ratio of about 100). The reaction was allowed to proceed for 15 h at 4° C. in the dark with gentle agitation. The solution was then treated with 10 mM $NaCNBH_3$ (aqueous) for 4 h at 4° C. with gentle agitation. The antibody was then spun through G-50 into SPDP buffer and concentrated to 1.3 mg/mL for the coupling reaction with RTA.

2. Reaction With RTA and Characterization of the Immunotoxin

RTA was concentrated to 6.4 mg/mL. and treated with 50mM DTT for 1 hour at room temperature to reduce sulfhydryls, then spun through G-50 into SPDP buffer. pH 7.5. The concentration of the reduced RTA was 4.75 mg/mL. A tenfold molar excess of RTA was added to IND1 (272 μL of 4.75 mg/mL RTA added to 0.5 mL 1.3 mg/mL IND1), inverted to mix and allowed to stand overnight at 4° C. without stirring. The presence of immunotoxin in the crude reaction was confirmed by SDS PAGE (Coomassie) and quantitated by densitometer scanning. The monoconjugate appeared to be 36% of the crude reaction mixture. The di-conjugate was present in about 10% yield. About 40% of the IND1 antibody was unreacted.

3. Purification of Immunotoxin

The impure reaction product was loaded on AcA-44 in SPDP. pH 7.5. Two peaks of protein were eluted from the column; the second peak containing antibody and immunotoxin was concentrated (100 μL. 1.77 mg/mL) and loaded onto a 0.8 mL column of Affigel Blue. After loading by gravity, the column was washed with 10 volumes of PBS, pH 7 at a flow rate of about 15 mL/h. A high salt, high pH step was then applied (0.1M phosphate, 0.5M NaCl, pH 8) to elute the immunotoxin. The immunotoxin was concentrated to about 60 μL (0.9 mg/mL) for SDS PAGE and activity assays (EIA and whole cell kill).

4. Activity Assay Results

Densitometry of the Coomassie stained SDS PAGE gel showed that the Affi-gel Blue purified material contained 10% free antibody, 20% monoconjugate and 9% di-RTA conjugate. As much as 55% of the stain was present as a diffuse high molecular weight band that resulted from periodate oxidation of the antibody.

EIA binding was determined for both the starting material and the final product. EIA for the immunotoxin was 23.3% (relative to 100% for unmodified IND1) and the whole cell kill activity was >200 ng/mL for the Affi-gel Blue purified material.

The foregoing is offered primarily for purposes of illustration. It will be readily apparent to those skilled in the art that variations and modifications in terms of the molecular structures, preparation procedures and reaction conditions may be made without departing from the spirit and scope of the invention.

What is claimed is:

1. A compound having the formula

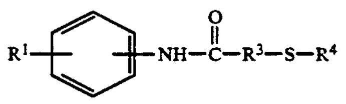

in which $R^1$ is a member selected from the group consisting of $NH_2$— and $NH_2$—NH—;

$R^3$ is a member selected from the group consisting of $C_1$–$C_{10}$ alkylene, phenyl-substituted $C_1$–$C_{10}$ alkylene, benzyl-substituted $C_1$–$C_{10}$ alkylene, and amino-substituted $C_1$–$C_{10}$ alkylene; and $R^4$ is a member selected from the group consisting of H, acetyl,

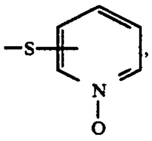,
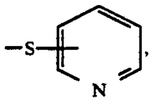,

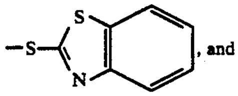, and 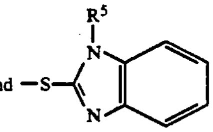

where $R^5$ is alkyl;

and analogs selected from the group consisting of water-soluble salts and water-soluble derivatives thereof.

2. A compound having the formula

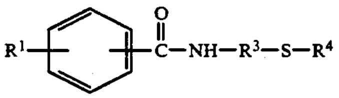

in which $R^1$ is a member selected from the group consisting of $NH_2$— and $NH_2$—NH—;

$R^3$ is a member selected from the group consisting of $C_1$–$C_{10}$ alkylene, phenyl-substituted $C_1$–$C_{10}$ alkylene, benzyl-substituted $C_1$–$C_{10}$ alkylene, and amino-substituted $C_1$–$C_{10}$ alkylene; and $R^4$ is a member selected from the group consisting of H, acetyl,

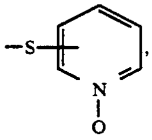,
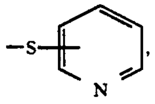,

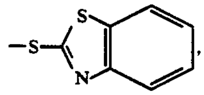, and 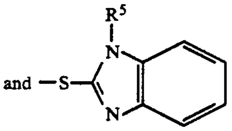

where $R^5$ is alkyl;

and analogs selected from the group consisting of water-soluble salts and water-soluble derivatives thereof.

3. A compound having the formula

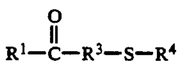

in which $R^1$ is a member selected from the group consisting of $NH_2$— and $NH_2$—NH—;

$R^3$ is a member selected from the group consisting of $C_1$–$C_{10}$ alkylene, phenyl-substituted $C_1$–$C_{10}$ alkylene, benzyl-substituted $C_1$–$C_{10}$ alkylene, and amino-substituted $C_1$–$C_{10}$ alkylene; and $R^4$ is a member selected from the group consisting of acetyl, 2-pyridylthio, 4-pyridylthio,

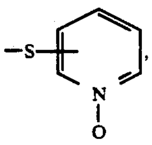, 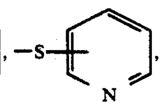,

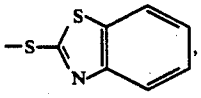, and 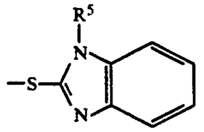

where $R^5$ is alkyl;

and analogs selected from the group consisting of water-soluble salts and water-soluble derivatives thereof.

4. A compound in accordance with claims 1, 2, or 3 in which $R^3$ is $C_1$–$C_{10}$ alkylene.

5. A compound in accordance with claims 1, 2, or 3 in which $R^4$ is a member selected from the group consisting of H, acetyl and

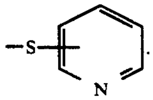.

6. A compound in accordance with claims 1 or 2 in which $R^3$ is $C_1$–$C_{10}$ alkylene, and $R^4$ is a member selected from the group consisting of H, acetyl and

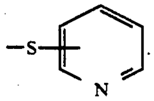.

7. A compound in accordance with claims 1 or 2 in which $R^4$ is a member selected from the group consisting of acetyl, 2-pyridylthio, and 4-pyridylthio.

8. A compound in accordance with claims 1, 2, or 3 in which said analogs are water-soluble salts thereof selected from the group consisting of acetate salts, trifluoroacetate salts, hydrohalide salts, and toluenesulfonic acid salts.

9. A compound in accordance with claims 1, or 2 in which $R^1$ is a meta- or para-position.

10. A compound in accordance with claims 1, or 2 in which $R^1$ is a at a para-position.

11. A compound having the formula

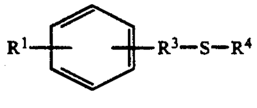

in which $R^1$ is 4-amino, $R^3$ is $-(CH_2)_3-$, and $R^4$ is acetyl.

12. A compound having the formula

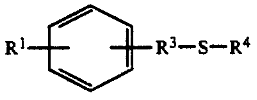

in which $R^1$ is 4-$NH_3^+$ $^-OOCCF_3$, $R^3$ is $-(CH_2)_3-$, and $R^4$ is acetyl.

13. A compound having the formula

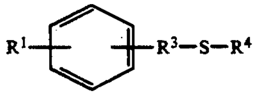

in which $R^1$ is 4-amino, $R^3$ is $-(CH_2)_4-$, and $R^4$ is acetyl.

14. A compound having the formula

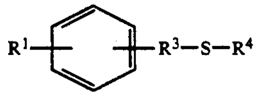

in which $R^1$ is 4-$NH_3^+$ $^-OOCCF_3$, $R^3$ is $-(CH_2)_4-$, and $R^4$ is acetyl.

15. A compound in accordance with claim 1 in which $R^1$ is 4-amino, $R^3$ is $-CH_2-$, and $R^4$ acetyl.

16. A compound in accordance with claim 1 in which $R^1$ is 4-$NH_3^+$ $^-OOCCF_3$, $R^3$ is $-CH_2-$, and $R^4$ is acetyl.

17. A compound in accordance with claim 1 in which $R^1$ is 4-amino, $R^3$ is $-(CH_2)_2-$, and $R^4$ is acetyl.

18. A compound in accordance with claim 1 in which $R^1$ is 4-$NH_3^+$ $^-OOCCF_3$, $R^3$ is $-(CH_2)_2-$, and $R^4$ is acetyl.

19. A compound in accordance with claim 2 in which $R^1$ is 4-amino, $R^3$ is $-(CH_2)_2-$, and $R^4$ is 2-pyridylthio.

20. A compound in accordance with claim 2 in which $R^1$ is 4-$NH_3^+$ $^-OOCCF_3$, $R^3$ is $-(CH_2)_2-$, and $R^4$ is 2-pyridylthio.

21. A compound in accordance with claim 2 in which $R^1$ is 4-hydrazino, $R^3$ is $-(CH_2)_2-$, and $R^4$ is acetyl.

22. A compound in accordance with claim 2 in which $R^1$ is 4-$NHNH_3^+$ $^-OOCCF_3$, $R^3$ is $-(CH_2)_2-$, and $R^4$ is acetyl.

23. A compound in accordance with claim 2 in which $R^1$ is 4-hydrazino, $R^3$ is $-(CH_2)_2-$, and $R^4$ is 2-pyridylthio.

24. A compound in accordance with claim 2 in which $R^1$ is 4-$NHNH_3^+$ $^-OOCCF_3$, $R^3$ is $-(CH_2)_2-$, and $R^4$ is 2-pyridylthio.

25. A compound in accordance with claim 3 in which $R^1$ is hydrazino, $R^3$ is $-CH_2-$, and $R^4$ is acetyl.

26. A compound in accordance with claim 3 in which $R^1$ is $NHNH_3^+$ $^-OOCCF_3$, $R^3$ is $-CH_2-$, and $R^4$ is acetyl.

27. A compound in accordance with claim 3 in which $R^1$ is hydrazino, $R^3$ is $-(CH_2)_2-$, and $R^4$ is 2-pyridylthio.

28. A compound in accordance with claim 3 in which $R^1$ is $NHNH_3^+$ $^-OOCCF_3$, $R^3$ is $-(CH_2)_2-$, and $R^4$ is 2-pyridylthio.

29. A compound in accordance with claim 1 in which $R^1$ is 4-amino, $R^3$ is $-(CH_2)_2-$, and $R^4$ is 2-pyridylthio.

* * * * *